United States Patent [19]

Disse et al.

[11] Patent Number: 5,552,161
[45] Date of Patent: Sep. 3, 1996

[54] LOW VISCOSITY, HIGHLY CONCENTRATED SURFACTANT SUSPENSION

[75] Inventors: Bernd Disse, Ingelheim am Rhein; Eberhard Weller; Robert Becker, both of Biberach, all of Germany

[73] Assignee: Dr. Karl Thomae GmbH, Biberach an der Riss, Germany

[21] Appl. No.: 432,386

[22] Filed: May 1, 1995

Related U.S. Application Data

[63] Continuation of Ser. No. 174,935, Dec. 28, 1993, abandoned, which is a continuation of Ser. No. 58,859, May 7, 1993, abandoned, which is a continuation of Ser. No. 881,450, May 12, 1992, abandoned, which is a continuation of Ser. No. 741,287, Aug. 7, 1991, abandoned, which is a continuation of Ser. No. 546,140, Jun. 29, 1990, abandoned.

[30] Foreign Application Priority Data

Jul. 4, 1989 [DE] Germany ............................ 39 21 954.2

[51] Int. Cl.$^6$ ..................................................... A61K 31/66
[52] U.S. Cl. ............................... 424/557; 514/75; 514/975
[58] Field of Search ............................... 424/557; 514/75, 514/975

[56] References Cited

PUBLICATIONS

Bligh & Dyev Canadian J. Biochemistry and Physiology 37(8):911–917 (1959).
Weber & Possmayer Biochemica & Biophysica Acta 796 (1984):83–91.
Davies et al Biochemica & Biophysica Acta 878 (1986):135–145.

*Primary Examiner*—Marianne M. Cintins
*Assistant Examiner*—Keith MacMillan
*Attorney, Agent, or Firm*—Robert P. Raymond; Alan R. Stempel; Mary-Ellen M. Devlin

[57] ABSTRACT

Low viscosity, highly concentrated surfactant suspensions for replacement therapy In diseases of the respiratory tract are described. The suspensions are characterised in that they contain calcium and/or magnesium ions bound to the surfactant and unbound in the suspension agent, as well as containing a certain amount of common salt.

9 Claims, 2 Drawing Sheets

LOW VISCOSITY, HIGHLY CONCENTRATED SURFACTANT SUSPENSION

This is a continuation of application Ser. No. 08/174,935, filed Dec. 28, 1993, abandoned which is a continuation of application Ser. No. 058,859, filed May 7, 1993, now abandoned, which is a continuation of application Ser. No. 881,450, filed May 12, 1992, now abandoned, which is a continuation of application Ser. No. 741,287, filed Aug. 7, 1991, now abandoned, which is a continuation of application Serial No. 546,140, filed Jun. 29, 1990, now abandoned.

The invention relates to low viscosity, highly concentrated surfactant suspensions for replacement therapy in respiratory tract diseases and processes for preparing them. The surfactant is a surface-active aggregate of phospholipids, neutral lipids and surfactant-associated hydrophobic proteins obtained from isolated natural pulmonary surfactant; however, the surfactant may also be obtained from synthetic sources in which case it is made up of synthetic lipids and optionally recombinant proteins.

A deficiency in pulmonary surfactant has been recognised to be a primary cause of respiratory distress syndrome in premature babies (Avery ME, Mead J. Surface properties in relation to atelectasis and hyaline membrane disease. Amer J Dis Child 97: 517–523 (1959)). The value of replacement therapy with natural surfactant is known from experimental and clinical studies (Van Golde, LMG, Batenburg JJ, Robertson B. The pulmonary surfactant system: biochemical aspects and functional significance. Physiol Rev 68: 374–455 (1988), Robertson B, Lachmann B. Experimental evaluation of surfactants for replacement therapy. Experimental Lung Research 14: 279–310 (1988)). Depending on the activity of the surfactant used or the judgement of the authors, individual doses of between 50 and 200 mg/kg were instilled by intratracheal route. Adult respiratory distress syndrome has certain parallels with respiratory distress syndrome in premature babies. In the opinion of a number of scientists, surfactant replacement offers a chance of therapy in this syndrome which has a high mortality rate (Lachmann B, Surfactant replacement in acute respiratory failure: Animal studies and first clinical trials, in B. Lachmann ed.: Surfactant replacement therapy in neonatal and adult respiratory distress syndrome. Springer-Verlag, Berlin 1988 pp 212–223). For this therapeutic use, high dosages of up to 400 mg/kg are proposed (Lachmann B, Surfactant replacement in acute respiratory failure: Animal studies and first clinical trials, in B. Lachmann ed.: Surfactant replacement therapy in neonatal and adult respiratory distress syndrome. Springer-Verlag, Berlin 1988 pp 212–223; Spragg RG, Richmann P, Gillard N, Merritt TA. The future for surfactant therapy of the adult respiratory distress syndrome, in B. Lachmann ed.: Surfactant replacement therapy in neonatal and adult respiratory distress syndrome. Springer-Verlag, Berlin 1988 pp 203–211).

In all applications, the loading of the patient's lungs with large quantities of liquid constitutes a problem. Enhorning treated his premature patients with 100 mg/kg of surfactant in the form of a 25 mg/ml suspension. This means that he administered 4 ml of liquid per kg of body weight (Enhorning G. Shennan A, Possmayer F, Dunn M, Chen CP, Milligan J. Prevention of neonatal respiratory distress syndrome by tracheal instillation of surfactant: A randomized clinical trial. Pediatrics 76: 145–153 (1985)). Robertson administered single doses of 200 mg/kg of a relatively highly concentrated suspension of 80 mg/ml (Noack G, Bergren P, Curstedt T. Grossmann G, Herin P, Mortensson W, Nilsson R, Robertson B, Severe neonatal respiratory distress syndrome treated with the isolated phospholipid fraction of natural surfactant. Acta Paediatr Scand 76: 697–705 (1987)). This means that a dosage of 2.5 ml/kg is administered. The highest concentrations were used by Morley, with synthetic surfactant (Ten centre study group. Ten centre trial of artificial surfactant (artificial lung expanding compound) in very premature babies. British Med J 294:991–996 (1987)). 100 mg/kg were given in the form of a 100 mg/ml suspension of crystals. Up to 400 mg/kg were required in 24 hours. A relatively favourable situation was achieved using a surfactant consisting of a surface active combination of phospholipids, neutral lipids and surfactant-associated hydrophobic proteins, obtained from isolated natural surfactant from bovine lungs, hereinafter referred to as SF-RI 1. 50 mg/kg were given as a 40 mg/ml suspension. This means the patients were given a volume of 1.2 ml/kg.

If these conditions are transferred to adult therapy, a dosage of 200 mg/kg, given as a 40 mg/ml suspension, would still mean that a patient with a body weight of 70 kg would have to be given 350 ml instilled by intratracheal route. This calculation showed that it is desirable to make the surfactant as concentrated as possible. This desire is limited by the high viscosity of surfactant suspensions with a concentration greater than 60 mg/ml. A high viscosity leads to problems in the administration and distribution of the surfactant and causes an increase in the resistance of the respiratory tract. Robertson achieved a level of 80 mg/ml by separating the neutral lipids from a surfactant obtained from pig lungs (Noack G, Bergren P, Curstedt T, Grossmann G, Herin P, Mortensson W, Nilsson R, Robertson B, Severe neonatal respiratory distress syndrome treated with the isolated phospholipid fraction of natural surfactant. Acta Paediatr Scand 76:697–705 (1987)). Morley used 100 mg/ml of crystallite suspension of synthetic lipids (British Med J 294: 991–996 (1987)). He achieved this high concentration at the cost of having to use ice-cooled suspending agents.

It has now been found, surprisingly, that even with loadings of surfactant of >60 mg/ml and storage at ambient temperature for several hours, the viscosity of the suspensions will remain below 30 mPas provided that a) the surfactant-lipid/protein preparation used contains a quantity of bound $Ca^{2+}$ and/or $Mg^{2+}$-ions of more than 25 mmol/mol, preferably more than 40 mmol/mol of organically extractable phospholipids, b) the suspending agent contains at least 1 mmol/l, preferably 2.5 to 3.5 mmol/l of $Ca^{2+}$ and/or $Mg^{2+}$-ions and c) at the same time the suspending agent contains at least 33 mmol/l, preferably 60 to 150 mmol/l of sodium chloride.

Water is generally used as the suspending agent. If only one of these factors is absent or if only one of these factors is present in too low a concentration, the viscosity of the suspension thus obtained increases dramatically at ambient temperature. If all three factors are observed, a low viscosity surfactant of high concentration which will remain stable for more than 12 hours even at ambient temperature can be prepared even from a vesicle lyophilisate. Such a surfactant suspension does not exhibit any dangerous increase in the resistance of the respiratory tract even with a very high surfactant content and is best suited for use or replacement therapy in diseases of the respiratory tract. A surfactant suspension of this kind means that the surfactant can be introduced by intratracheal route in high doses without overloading the lungs with water or causing any other negative effects, e.g. as a result of an increase in viscosity.

Whereas the surfactant suspensions known hitherto have been highly viscous even with a concentration of 60 mg of surfactant per ml, it is now possible, using the procedure according to the invention, to prepare suspensions with concentrations of 200 mg/ml; for therapeutic use surfactant concentrations of 150 mg/ml of suspension are particularly suitable, for example. Surfactant suspensions of lower viscosity can easily be obtained, if desired, by diluting the suspensions according to the invention with suspending agents according to the invention as desired.

The charging of the organically extractable phospholipids with $Ca^{2+}$ and/or $Mg^{2+}$ ions, after these phospholipids have been isolated from the lavages of the lungs of cattle or pigs, for example, is carried out by giving the aqueous phase an excess of $Ca^{2+}$ or $Mg^{2+}$-ions during extraction of the aqueous phase with chloroform, for example. Depending on the way in which the preparation is worked up, there is an upper limit of $Ca^{2+}$ or $Mg^{2+}$-ions of about 70 mmol $Ca^{2+}$ or $Mg^{2+}$ per mol of phospholipid. If a phospholipid mixture or phospholipid/protein mixture has too low a charge of $Ca^{2+}$ or $Mg^{2+}$-ions, like the 13 mmol $Ca^{2+}$/mol phospholipid-protein mixture in batch B (Table 1), this batch can subsequently be charged with the deficient $Ca^{2+}$ or $Mg^{2+}$-ions in organic solutions. This is done for example by adding $CaCl_2$ dissolved in methanol. Generally, it can be said that all known dry lipids can be charged with $Ca^{2+}$ and/or $Mg^{2+}$-ions and processed into low viscosity suspensions.

The calcium and magnesium ions are supplied in the form of soluble calcium and magnesium salts. It is preferable to use calcium chloride or magnesium chloride for this purpose; however, other physiologically acceptable, water-soluble calcium and/or magnesium salts can be used, such as calcium or magnesium sulphate, calcium nitrite, calcium lactate, calcium sorbate, calcium ascorbate, calcium gluconate, calcium lactogluconate, magnesium hydrogen citrate, magnesium dihydrogen glutamate or magnesium citrate.

The surfactant material which constitutes the starting product for the low viscosity, highly concentrated surfactant suspensions is prepared in accordance with the method described by Yu et al. (Lipids 18: 522–529 (1983)). A substantial deviation from this method is the use of solvents or suspending agents which contain calcium or magnesium throughout the entire process. Cattle lungs are washed out with a saline solution containing 3 mmol/l of $Ca^{2+}$ and/or $Mg^{2+}$-ions. The surfactant is centrifuged out from a solution which contains 6 to 12 mmol/l of $Ca^{2+}$ and/or $Mg^{2+}$-ions, preferably $Ca^{2+}$ ions. Purification by density gradient centrifugation using glucose at a density of between 1.05 and 1.15 g/ml is again carried out in the presence of 3 to 8 mol/l of $Ca^{2+}$ and/or $Mg^{2+}$-ions. Purification is followed by further purification by distribution in a system of chloroform, methanol and water according to Bligh and Dyer (cf. Can. J. Biochem. Physiol. 37: 911–917 (1959)) using an aqueous phase with 3 to 10 mmol/l of $Ca^{2+}$ and/or $Mg^{2+}$-ions, preferably 6 mmol/l. The organic phase is subsequently concentrated by evaporation in vacuo at ambient temperature and the residue is dried and finally ground up. Alternatively, the organic phase may also be freeze-dried. In this case, the product obtained is stable for storage for a longer period (at least 3 years at refrigerator temperature). The finely powdered dry lipid thus obtained is suspended in an aqueous solution containing the quantities of common salt and $ca^{2+}$ and/or $Mg^{2+}$ salts according to the invention, by vigorous shaking until the desired lipid concentration is obtained. A suspension prepared in this way can also be stored at refrigerator temperatures for a few days and can be administered by intratracheal route as required.

The suspending agent should contain more than 1 mmol/l, preferably 2.5 to 3.5 mmol/l, of $Ca^{2+}$ and/or $Mg^{2+}$-ions and more than 33 mmol/l, preferably 75 mmol/l and not more than 150 mmol/l, of common salt.

INVESTIGATIONS OF VISCOSITY WITH DIFFERENT SURFACTANT PREPARATIONS

Equipment and Method

Figure 1:
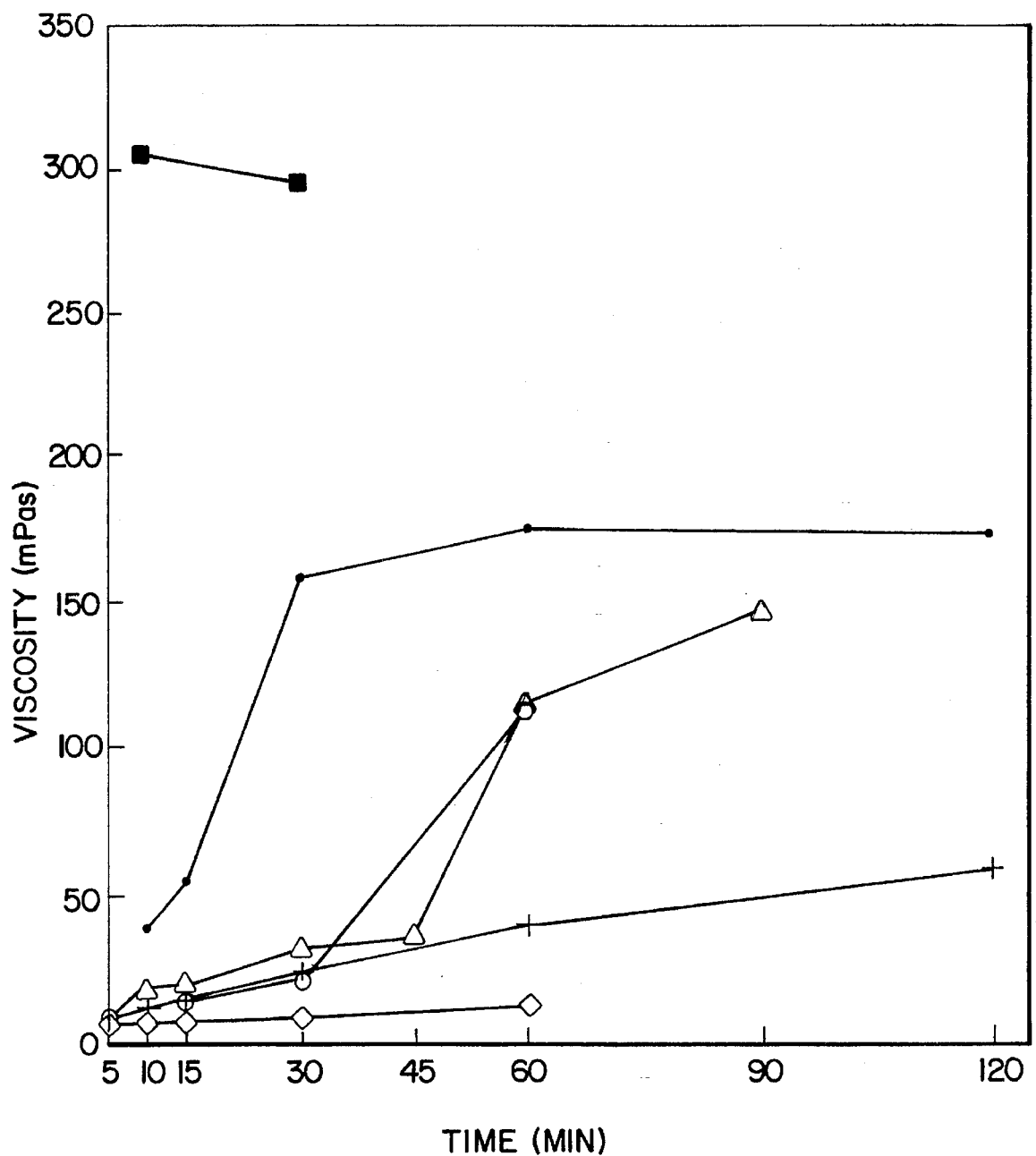
FIG. 1 shows the results of viscosity tests of freshly prepared surfactant suspensions over time.

For the tests which follow, an extracted surfactant obtained from lavage of bovine lungs was used as the starting material (hereinafter referred to as SF-RI 1). The procedure used is essentially a modified and improved form of the method of Yu et al. (Yu S, Harding PGR, Schmith N, Possmayer F. Bovine pulmonary surfactant: chemical composition and physical properties. Lipids 18: 522–529 (1983)). Major deviations from this procedure were the use of calcium-containing solvents throughout the entire process: the washing out of the cattle lungs was carried out using a common salt solution and the lavage liquid was adjusted to a calcium content of 6 mmol/l (using $CaCl_2$). Surfactant was centrifuged out of a solution containing 9 mmol/l of calcium. Purification using a glucose density gradient was carried out in the presence of 6 mmol/l of calcium. The most important step was that the purification was carried out by distribution in a chloroform/methanol/water system according to Bligh and Dyer (Can. J. Biochem. Physiol. 37:911–913 (1959)), also using an aqueous phase which contained 6 mmol/l of calcium chloride.

After phase separation had been carried out the organic phase was rotary-evaporated to dryness at ambient temperature and then dried in vacuo. The water content according to Karl Fischer should be less than 3% if possible. The material was reduced to a particle size of about 160 µm by screening.

For the tests, this finely powdered dry lipid was suspended in aqueous solutions containing varying amounts of calcium chloride and sodium chloride in ampoule water by vigorous shaking. The concentration of the suspensions was between 60 and 250 mg/ml.

The viscosity of these suspensions after storage at ambient temperature for specific lengths of time was determined using a capillary viscometer. The procedure used was a modified method of measurement by capillary viscometer described by Weller et al. in Wiener Medizinische Wochenschrift suppl. 33: 7–12 (1975) and by Weller in "Viskosimetrie inhomogener Flüssigkeiten", Dustri Verlag München, pp 21–41. A brief explanation will now be given. The sample contained in a syringe is forced through a measuring capillary at a defined constant speed. Inhomogeneities can also be detected. The shear speed is known and constant. Calibration is performed using calibrating oils. The pressure in front of the capillary is a measurement of the viscosity and is continuously recorded using a pen recorder.

Towards the end of the test period, some suspensions were converted into vesicle suspensions by the use of ultrasound energy (Branson Ultrasound apparatus, Micro-tip, 20 Watts, 2 min/ml, cooling with ice water).

Suspensions prepared by shaking freeze-dried solutions or vesicle dispersions were also investigated. Surfactant was dispersed in ampoule water in concentrations of about 40 mg/ml, if necessary by the use of ultrasound energy, or dissolved in other suitable solvents such as tert.-butanol in concentrations of about 40 to 250 mg/ml. The suspensions or solutions were then freeze-dried. The cake which formed was broken up and the resulting powder was processed again.

Alternative forms of the process for preparing SF-RI I were also included in the tests. The surfactant batch B (see Table 1) was prepared without the addition of calcium chloride to the irrigation and cleaning media.

The calcium was measured by atomic absorption photometry after suitable dilute suspensions of surfactant had been burned in an acetylene flame at about 3000° C. (Zeiss FL6). At these temperatures, even calcium bound in a protein matrix is liberated and accurately measured.

The relative effectiveness of the surfactant suspension on immature rabbit foetuses was determined by comparison with a reference standard. A dose-activity curve was plotted with 3 doses for the batch to be tested and for the reference standard (see FIG. 2). Using generally known statistical criteria (analysis of covariants) it was shown that the highly concentrated suspension containing $Ca^{2+}$-ions according to the invention was not significantly different in its effect from the low concentration vesicle dispersion at similar doses.

Results and Discussions

The calcium content of representative batches of SF-RI 1 is shown in Table 1.

high contents of bound calcium are very important for the properties of SF-RI 1.

Table 1 and FIG. 1 also contain the results of the tests on the viscosity of freshly prepared surfactant suspensions in the course of time. When a "calcium-poor" i.e. a conventional surfactant (B), was suspended in a solution of 75 mmol/l of common salt and 3 mmol/l of calcium chloride, the viscosity rapidly increased at ambient temperature and after only 30 minutes was in excess of 150 mPas. This means that the surfactant suspension had taken on a creamy consistency. This suspension is clinically unuseable for intratracheal installation.

When a surfactant with a high bound calcium content (A, A' and C) was suspended in a solution containing 3 mmol/l of calcium chloride, the viscosity also increased very rapidly. Even when suspended in a saline solution of 75 mmol/l, the viscosity reached approximately 150 mPas after 90 minutes storage at ambient temperature. Suspension in a solution of 75 mmol/l of common salt plus 1 mmol/l of calcium chloride resulted in a slow and reduced increase in viscosity.

Very satisfactory results were obtained by suspending "calcium-rich" surfactant in a solution of 75 mmol/l of common salt plus 3 mmol/l of calcium chloride: here, even after lengthy storage, the viscosity did not exceed 25 mPas. Comparable results were achieved by suspending "calcium-rich" surfactant lyophilisates in a solution of 75 mmol/l of common salt plus 3 mmol/l of calcium chloride (batch C). Here again, the viscosity did not exceed 25 mPas even after lengthy storage at ambient temperature for 16 hours. only when ultrasound energy was applied did the viscosity increase to 220 mPas.

TABLE 1

| | | | | Viscosity of a suspension of 150 mg of surfactant per ml of suspension | | | | | | | | |
|---|---|---|---|---|---|---|---|---|---|---|---|---|
| | | Suspension medium | | Storage at ambient temperature up to (between preparation of the suspension and measurement of viscosity) | | | | | | | | |
| Preparation | $Ca^{2+}$- content [mmol/mol] | $CaCl_2$ [mmol/l] | NaCl [mmol/l] | 5 min | 10 min | 15 min | 30 min | 45 min | 60 min | 90 min | 120 min | 16 h |
| | | | | | | | | [mPas] | | | | |
| A | 48 | 3 | 0 | | 304 | | 295 | | | | | |
| A | 48 | 0 | 75 | 11 | 20 | 20 | 34 | 37 | 118 | 148 | | |
| A | 48 | 1 | 75 | 9 | | 15 | 22 | | 113 | | | |
| A | 48 | 3 | 75 | 7 | 7 | 8 | 9 | | 13 | | | |
| A' | 58 | 3 | 75 | | 21 | 22 | 24 | | | 22 | 24 | |
| B | 13 | 3 | 75 | | 40 | 56 | 160 | | 177 | | 176 | |
| B | 13 | 12 | 75 | | 13 | | 25 | | 40 | | 60 | |
| C | 42 | 0 | 75 | | 181 | 184 | | | 202 | 219 | | |
| C | 42 | 3 | 75 | 6 | 8 | | 9 | 14 | 16 | | | 21 |
| C | 42 | 3 | 75 | Viscosity after ultrasonic treatment 2 min/ml, 20 Watt Branson ultrasonic equipment with micro-tip: 222 mPas | | | | | | | | |

A: powdered surfactant, 160 μm particle size, prepared as described in the text by modification of the method of Yu et al., Lipids 18, 522–528 (1983)
A': powdered surfactant, undefined particle size, prepared as in A,
B: powdered surfactant, undefined particle size, prepared as in A, but without the addition of $Ca^{2+}$ during the working up process,
C: lyophilised surfactant, preparation of the lipid-protein mixture as in A.

The results show that all the batches which correspond to the method of production described, contain quantities of bound calcium of more than 40 mmol/mol of lipid-extractable phosphate. Batch (B), worked up without the addition of calcium, on the other hand, contains only 13 mmol/mol. It is consequently within the range of published values of calcium contents in extracted pulmonary surfactant which do not exceed 16 mmol/mol (Weber MJ, Possmayer F. Calcium interactions in pulmonary surfactant. Biochim Biophys Acta 796: 83–91 (1984)). As is shown hereinafter, these Suspension of the "Ca-poor" lipid (B) in a solution with a non-physiologically high Ca concentration of 12 mmol/l plus 75 mmol/l of NaCl brought about a slower and lesser increase in viscosity. Nevertheless, after 120 minutes, a value of 60 mPas was achieved. The concentration of 12 mmol/l was calculated so that the final concentration obtained (sum of the $Ca^{2+}$ contents in the suspending agent and in the lipid) came to the same value as if A, A' or C were suspended in 3 mmol/l of Ca-containing solution. This variant of providing high Ca-contents in the suspending agent is less favourable in its results and cannot be used for the in vivo applications envisaged because non-physiologically high Ca-concentrations are used in the suspending agent which may trigger bronchoconstriction.

The results show that, surprisingly, three factors are essential for achieving highly concentrated but low viscosity surfactant suspensions: the surfactant lipid/protein preparation used must have a high content of bound calcium, preferably more than 25 mmol per mol of organically extractable phosphlipids. The suspending agent must contain both NaCl and also $CaCl_2$ dissolved therein, preferably in concentrations of 75 mmol/l and 3 mmol/l respectively. The tests in Table 1 show that if only one of these factors is absent the viscosity of the suspensions at ambient temperature will rise dramatically after a short time. However, if all three factors are maintained, a low viscosity surfactant with a high concentration which remains stable for more than 12 hours even at ambient temperature can be prepared even from a vesicle lyophilisate. This type of surfactant suspension is suitable for therapeutic use. FIG. 1 also shows the curve of the viscosity of a suspension with 150 mg of surfactant per ml as a function of the $Ca^{2+}$ concentration bound to surfactant and dissolved in the suspending agent with and without added salt.

Figure 2:
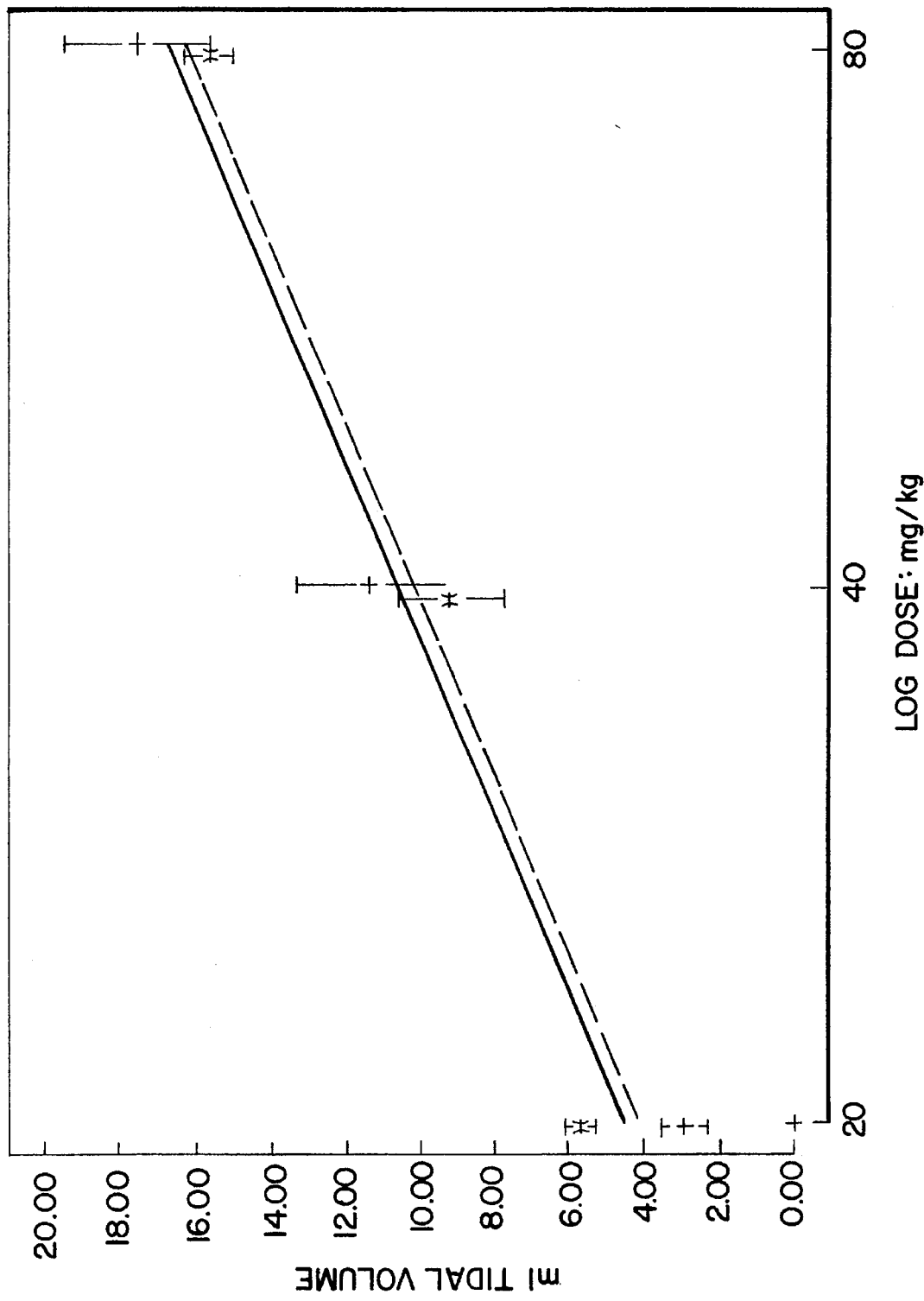
FIG. 2 shows that the addition of calcium in the concentration range of 3 mmol/l in the suspending medium has no effect on efficacy degree in immature rabbit foetuses.

The effectiveness of surfactant on the physiology of respiration can be investigated on immature rabbit foetuses (Robertson B, Lachmann B., Experimental evaluation of surfactants for replacement therapy. Experimental Lung Research 14, 279–310 (1988)). These animals with immature lungs can only be ventilated after replacement therapy with surfactant. By direct comparison of two batches of animals from the same litter, the relative potency is determined, i.e. the quantity which has the same effectiveness. In this animal-experimental model it was found that the addition of calcium in a concentration of around 3 mmol/l in the suspending agent had no effect on the degree of efficacy (FIG. 2). The relative potency was unchanged.

In FIG. 1 the individual curves show the course of the change in viscosity [mPas] in time (minutes). The individual curves relate to the following series of tests:

- ■ highly concentrated bound $Ca^{+2}$, suspension medium contains 3 mmol $Ca^{2+}$ but no NaCl
- ▲ highly concentrated bound $Ca^{+2}$, suspension medium contains 75 mmol NaCl but no $Ca^{2+}$
- ● highly concentrated bound $Ca^{+2}$, suspension medium contains 1 mmol $Ca^{2+}$ and 75 mmol NaCl
- ◆ highly concentrated bound $Ca^{+2}$, suspension medium contains 3 mmol $Ca^{2+}$ and 75 mmol NaCl
- ●— lower concentration of bound $Ca^{+2}$, suspension medium contains 3 mmol $Ca^{2+}$ and 75 mmol NaCl
- + low concentration of bound $Ca^{+2}$ suspension medium contains 12 mmol $Ca^{2+}$ and 75 mmol NaCl FIG. 2 shows that the addition of calcium in the concentration range of 3 mmol/l in the suspending medium has no effect on the degree of efficacy in immature rabbit foetuses. The continuous line shows the situation in the absence of calcium chloride whilst the dotted line indicates the situation in the presence of 3 mmol of $ca^{2+}$ ions (in the form of $CaCl_2$) per liter; the measured potency is shown as the tidal volume achieved at 3 KPa respiration pressure as a function of log dose.

The Examples which follow describe the preparation of some suspensions according to the invention:

EXAMPLE 1

A surfactant obtained by extraction from cattle lungs with organic solvents is used. It consists of about 88% phospholipids, 4% cholesterol, 1% surfactant-associated hydrophobic proteins, 0.6% free fatty acids, as well as triglycerides and bound calcium. The average relative molecular mass of the phospholipids is approximately 760 D. The substance is a yellow amorphous powder which is insoluble in water but readily soluble in non-polar solvents such as chloroform; it can easily be suspended in water by shaking or by the use of ultrasonic energy. Upwards of a concentration of 5% by weight the suspensions are visibly viscous. The preparation, isolation and working up are carried out in accordance with the method described in Lipids 18: 522–529 (1983), with the additional introduction of $Ca^{2+}$ ions. If necessary the calcium content can subsequently be corrected as desired, e.g. by adding calcium chloride dissolved in methanol in the calculated amount to the surfactant dissolved in organic solvent, e.g. chloroform.

1.5 g of the finely powdered, screened surfactant described above or a substance obtained by freeze-drying a surfactant dissolved in tert.-butanol or cyclohexane are mixed with 8.5 ml of a suspending agent, preferably saline solution, containing 75 mmol/l of common salt and 3 mmol/l of calcium chloride, preferably in an injection vial. The injection vial is then shaken and the surfactant is thus suspended. The suspension is drawn up in an injection syringe with an injection cannula size 1 (20 G) and then injected back into the vial through a size 18 cannula (26 G). The forcing back of the suspension into the vial through the thin cannula is merely a safety measure to ensure that the suspension is free from lumps. The suspension is administered, for example, through a catheter in the umbilical vein into the tracheal tube of the patient on a ventilator.

EXAMPLE 2

2.5 g of the finely powdered, screened surfactant are combined with 7.5 ml of suspending agent (saline solution) containing 150 mmol/l of common salt and 3.5 mmol/l of calcium chloride. Further processing is carried out as described in Example 1.

We claim:

1. An aqueous pulmonary surfactant suspension for use in replacement therapy in diseases of the respiratory tract, having a surfactant lipid/protein concentration of from about 60 to about 200 mg/ml and a viscosity of from about 6 to about 40 mPas, comprising:

a) natural or artificial surfactant lipid/protein, having calcium and/or magnesium ions bound thereto in a ratio of from 25 to 70 mmol per mol of organically extractable phosphlipid, suspended in an aqueous medium comprising about 1 to about 3.5 mmol/l of unbound calcium and/or magnesium ions, and b) additionally comprising sodium chloride in a concentration of from about 33 to about 150 mmol/l, wherein the natural or artificial surfactant lipid/protein is present in the aqueous medium at a total concentration of from about 60 to about 200 mg/ml.

2. The surfactant suspension according to claim 1, wherein the surfactant lipid/protein used has a ratio of bound calcium and/or magnesium ions of about 40 to about 70 mmol per mol of organically extractable phospholipids and the aqueous medium comprises about 2.5 to about 3.5 mmol/l of unbound calcium and/or magnesium ions and about 60 to about 150 mmol/l of sodium chloride.

3. The surfactant suspension according to claim 2, wherein the aqueous medium comprises 75 mmol/l of sodium chloride.

4. The surfactant suspension according to claims 1, 2 or 3, wherein the surfactant lipid/protein has calcium ions bound thereto in a ratio of about 42 to about 58 mmol per mol of organically extractable phosphlipid and the aqueous medium comprises calcium chloride in a concentration of 3 mmol/l and sodium chloride in a concentration of 75 mmol/l.

5. A process for preparing an aqueous pulmonary surfactant suspension, suitable for use in replacement therapy in diseases of the respiratory tract, having a surfactant lipid/protein concentration of from about 60 to about 200 mg/ml and a viscosity of from about 6 to about 40 mPas, which method comprises:

a) irrigating cattle lungs with an aqueous sodium chloride solution to obtain a lavaged liquid surfactant lipid/protein, b) adjusting the lavage liquid to a calcium and/or magnesium ion concentration of 3 mmol/l, and centrifuging the surfactant lipid/protein out of a solution of comprising $Ca^{2+}$ or $Mg^{2+}$ ions in a concentration from about 6 to about 12 mmol/l, c) performing a first purification by means of a glucose density gradient in the presence of $Ca^{2+}$ and/or $Mg^{2+}$ ions in a concentration of about 3 to about 8 mmol/l, d) performing a second purification, by means of an extraction followed by phase separation, using a system comprising organic solvent/alcohol/water wherein the aqueous phase comprises from about 3 to about 10 mmol/l of $Ca^{2+}$ and/or $Mg^{2+}$ ions, such that the product collects in the organic phase, e) concentrating and drying the organic phase from the previous step to yield purified, dry, lipid/protein, f) grinding the dry lipid/protein to yield a fine powder, and g) suspending the finely powdered lipid/protein in an aqueous medium comprising $Ca^{2+}$ and/or $Mg^{2+}$ ions in a concentration from 1 to 3.5 mmol/l and sodium chloride in a concentration from about 33 to about 150 mmol/l.

6. The process according to claim 5, wherein the extraction and separation of step d) is carried out with a system comprising chloroform/methanol/water wherein the aqueous phase comprises from about 3 to about 10 mmol/l of $Ca^{2+}$ and/or $Mg^{2+}$ ions.

7. The process according to claim 5, wherein the finely powdered dry lipid/protein is suspended in an aqueous medium which comprises from about 2.5 to about 3.5 mmol/l of $Ca^{2+}$ ions and from about 60 to about 150 mmol/l of sodium chloride.

8. The process according to claim 5 wherein, in step e), the concentrating and drying the organic phase is accomplished by freeze-drying.

9. A process for preparing a dry, finely divided powdered, pulmonary surfactant material, suitable for preparing a surfactant suspension having a viscosity from about 6 to about 40 mPa and a surfactant lipid/protein concentration from about 60 to about 200 mg/ml, which method comprises:

a) irrigating cattle lungs with an aqueous sodium chloride solution to obtain a lavaged liquid surfactant lipid/protein solution, b) introducing calcium and/or magnesium ions to the lavaged liquid solution, and centrifuging the surfactant lipid/protein out of the solution of comprising $Ca^{2+}$ or $Mg^{2+}$ ions, c) perforating a first purification by means of a density gradient centrifugation in the presence of $Ca^{2+}$ and/or $Mg^{2+}$ ions, d) performing a second purification by extraction followed by phase separation using a system comprising organic solvent/alcohol/water wherein the aqueous phase comprises from about 3 to about 10 mmol/l of $Ca^{2+}$ and/or $Mg^{2+}$ ions, such that the product collects in the organic phase, e) concentrating and drying the organic phase form the previous step to yield purified dry lipid/protein, and f) grinding the dry lipid/protein to yield a fine powder.

* * * * *